United States Patent
Karwei

(10) Patent No.: US 9,039,703 B2
(45) Date of Patent: May 26, 2015

(54) ENDOSCOPIC SURGICAL INSTRUMENT

(75) Inventor: Dietmar Karwei, Ofterdingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 783 days.

(21) Appl. No.: 13/264,590

(22) PCT Filed: Mar. 26, 2010

(86) PCT No.: PCT/EP2010/001942
§ 371 (c)(1),
(2), (4) Date: Oct. 24, 2011

(87) PCT Pub. No.: WO2010/118818
PCT Pub. Date: Oct. 21, 2010

(65) Prior Publication Data
US 2012/0035607 A1 Feb. 9, 2012

(30) Foreign Application Priority Data

Apr. 16, 2009 (DE) .................... 10 2009 017 636

(51) Int. Cl.
A61B 18/18 (2006.01)
A61B 17/3203 (2006.01)
A61B 18/14 (2006.01)
A61B 17/00 (2006.01)

(52) U.S. Cl.
CPC ......... *A61B 17/3203* (2013.01); *A61B 18/1492* (2013.01); *A61B 2017/00269* (2013.01); *A61B 2018/1497* (2013.01)

(58) Field of Classification Search
USPC .............................. 606/46, 37–49
See application file for complete search history.

(56) References Cited

U.S. PATENT DOCUMENTS

| 6,511,493 B1 | 1/2003 | Moutafis et al. |
| 2004/0176761 A1* | 9/2004 | Desinger .......................... 606/50 |
| 2004/0210284 A1 | 10/2004 | Okada |
| 2004/0230190 A1* | 11/2004 | Dahla et al. ..................... 606/41 |
| 2009/0018602 A1 | 1/2009 | Mitelberg et al. |
| 2009/0069805 A1* | 3/2009 | Fischer et al. .................. 606/42 |
| 2009/0157114 A1* | 6/2009 | Fischer et al. ................. 606/192 |

FOREIGN PATENT DOCUMENTS

| DE | 3704410 A1 | 8/1987 |
| DE | 10 2004 020 855 A1 | 11/2005 |
| DE | 10 2005 038 694 A1 | 10/2006 |
| EP | 0 280 972 A1 | 9/1988 |
| EP | 1 148 770 A2 | 10/2001 |
| EP | 1 522 269 A1 | 4/2005 |
| EP | 1 929 968 A1 | 6/2008 |
| JP | 2000-262528 A | 9/2000 |
| JP | 2003-520078 A | 7/2003 |

(Continued)

*Primary Examiner* — Paula J Stice
(74) *Attorney, Agent, or Firm* — Dickstein Shapiro LLP

(57) ABSTRACT

An endoscopic surgical instrument including a fluid jet device and an electrode device. The fluid jet device includes a pipe section with a nozzle on one distal end for a dissection and/or a needleless injection by means of a fluid and the electrode device is for cutting and/or coagulating tissue, the pipe section forming the electrode device. The surgical instrument further includes an insulating device attached to the distal end of the pipe section such that the tissue can only be brought into electrically conductive contact with a peripheral region of the pipe section and not with the distal end of the pipe section.

15 Claims, 2 Drawing Sheets

(56) References Cited

FOREIGN PATENT DOCUMENTS

| JP | 2005-110861 A | 4/2005 |
| JP | 2007-534395 A | 11/2007 |
| JP | 2008-535591 A | 9/2008 |
| WO | WO 2005/104965 A1 | 11/2005 |
| WO | WO 2006/108480 A1 | 10/2006 |

* cited by examiner

ENDOSCOPIC SURGICAL INSTRUMENT

FIELD OF THE DISCLOSED EMBODIMENTS

The disclosed embodiments relate to an endoscopic combination surgical instrument for water jet surgery and RF surgery, and in particular an endoscopic combination surgical instrument for endoscopic mucosa elevation and mucosa resection.

BACKGROUND

The excision of tumors that cover a large area in the gastrointestinal tract and that are restricted to the mucosa should take place in one session, if possible, and should be complete, if possible. This is usually done using a loop or cap technique, by means of which essentially circular resectates having different sizes that are strictly a function of the loop or cap diameter are obtained. Large-area tumors having a diameter greater than 8 cm can be ablated only in partial steps.

In order to perform such a total operation, publication DE 10 2005 038 694 A1 has suggested an endoscopic instrument that combines a device for water jet surgery with a device for RF surgery to be handled as a unit. As a result of this, a multifunctional instrument is provided that is intended to combine the advantages of water jet surgery with those of RF surgery. The instrument allows a metered injection of an NaCl solution under the mucosa in order to lift the mucosa off the muscularis. Furthermore, this instrument also allows a separation with the use of the fluid jet. For separating the submucosa, the device is used for RF surgery. Thus, one and the same instrument can be used for performing two successive operative steps—without any instrument change. The design of this instrument provides for two channels extending from the proximal end to the distal end of the instrument, i.e., a first channel for the cutting fluid and a second channel accommodating the RF surgical instrument so that it can be moved. Both channels are jacketed by a shared protective sheath and thus form a unit. The distal end of the first channel has a nozzle in order to be able to eject the fluid jet at sufficient speed or with sufficient energy in order to be able to achieve said cutting effect.

During surgery using this instrument, it is necessary to work with two different instruments projecting on the distal end of the instrument. Though these instruments existing in a combined instrument, the full attention of the surgeon is still required. Furthermore, this instrument may be expensive to manufacture because specifically dedicated "instruments" are necessary for the nozzle of the water jet surgical device, on the one hand, and for the RF surgical device, on the other hand.

Publication EP 0 280 972 A1 discloses a surgical instrument for open surgery, namely, a handle for surgical use, the handle including a combination of a fluid jet cutting instrument and an RF coagulation instrument, thus allowing the immediate coagulation—i.e., closure, of vessels that are bleeding after having being cut with the fluid jet—by means of an instrument using RF. To accomplish this, the handle comprises, on its distal end, a coagulation electrode that, at the same, time accommodates an outlet nozzle for the cutting fluid. With this instrument, it is not possible to operate endoscopically because an unwanted contact of tissue within the body cavity cannot be avoided. Additionally, a cutting with RF current is not possible using this instrument. Furthermore, with this instrument, it is not possible to mark planned cutting edges prior to the actual dissection, which thus requires planning and recording, on the one hand, and cutting, on the other hand, to occur in two phases, in order to ensure greater safety.

Considering the aforementioned prior art, it is the object of the disclosed embodiments to provide an endoscopic surgical instrument that is simple in design and is easy to handle, so that, in particular, a mucosa elevation and resection can be performed in a single procedural step. Furthermore, it is the object of the invention to provide an method for the manufacture of such an instrument.

SUMMARY

Disclosed embodiments include an endoscopic surgical instrument including a fluid jet device having a pipe section with a nozzle at a distal end for a dissection and/or a needleless injection by means of a fluid, and also including an electrode device for cutting and/or coagulating a tissue by means of RF current, where the pipe section of the fluid jet device is the electrode device and an insulating device is attached to the distal end of the pipe section in such a manner that the tissue can only be brought into electrically conductive contact with a peripheral region and not with the distal end of the pipe section.

In the disclosed embodiments, a wedge of the water line necessary for water jet surgery (e.g., the pipe section) is configured as an RF surgical instrument (i.e., it is also configured for cutting). However, it is not the distal end of the pipe section (as in the subject matter of EP 0 280 972 A1) that is used, but is instead the exterior jacket of the pipe section. In order to ensure this, the distal end of the pipe section is secured by the insulating device against an electrically conductive contact of tissue, so that—even in a tight space during endoscopic surgery—a minimization of the surgical risks is ensured.

In one example embodiment, the insulating device is disposed to act as a mechanical preparation device for the preparation of tissue. The insulating device could have the shape of a hook; however, in general, it is sufficient to make the insulating device disk-shaped because the tissue to be treated is relatively soft.

Furthermore, in another example embodiment, a line for conveying the inert gas to the tissue is provided. In this case, the inert gas can act as a "protective gas" in such a manner that there is no burning of the tissue because of the displacement of oxygen during these cutting and coagulation steps.

If the region between tissue and instrument is filled with an inert gas, tissue can also be coagulated in accordance with the basically known "APC" (argon plasma coagulation) principle. To accomplish this, the electrode device may include a concentrating element that, in one example embodiment, has a beveled or pointed form in order to enhance a field strength generated by an electrical charge of the electrode device. This concentrating device may include, for example, a beveled edge region of the nozzle because a considerable increase of the field strength already occurs due to such an edge. Alternatively or additionally, at least one needle-shaped arrangement may be provided, this arrangement being in electrically conductive communication with the electrode device and, in one example embodiment, being made in one piece with the electrode device.

In one example embodiment, an electrically insulating sheathing device is provided that is arranged so as to movably enclose the electrode device such that the electrode device can be slid back into the sheathing device or out of said sheathing device. Consequently, considering this embodiment, when the electrode device is retracted into the sheathing device, contact with the tissue is no longer possible and the instrument is then strictly a water jet surgical instrument. Only when it is pushed out of the sheathing device is the electrode device exposed and can be used for RF surgery as well as for the strictly mechanically preparation (by means of the appropriately designed insulating device). Furthermore, if the instrument is used for an "APC application", an electrically conductive contact of the tissue by the electrode device is prevented. In this case, the instrument thus becomes strictly an "APC probe".

In one example embodiment, stop devices are provided to simplify handling in such a manner that any retraction or projection can be delimited by said stop devices. These stop devices can be adjusted in such a manner that the degree to which the electrode device can be moved out of the sheathing device can be accomplished without increased care on the part of the surgeon.

The supply of the electrode device with RF current can occur via a separate electrical supply line. Preferably, however, the fluid jet device is provided with an electrically conductive line section for supplying the fluid and the RF current, said section being connected with the pipe section in a sealed and electrically conductive manner. As a result of this, the size of the instrument can be minimized as to its requirements of space, this being of particular importance in endoscopic applications.

In one embodiment, the pipe section that can be brought into tissue contact includes a material having a melting point above approximately 2000° C., and is preferably made of tungsten. In contrast with the suggestion made in EP 0 289 972 A1, it has been found that, with the use of a stainless steel, significant burning and other disadvantageous effects can occur.

The pipe section may be manufactured of tungsten by means of a powder injection molding (PIM) process. Such powder injection molding processes are known in the art and are subdivided into two manufacturing processes, namely "metal powder injection molding" (MIM—metal injection molding) and "ceramic powder injection molding" (CIM—ceramic injection molding). With the use of these methods it is possible to implement technically high-quality components, even in the micro-range, in that efficient manufacturing processes are employed while excellent tolerances are maintained. This is achieved, even though the shrinkage in powder injection molding is on the order of around 20%, because the process can be reproduced well.

This technology may also be used for the manufacture of the insulating device, i.e., by using ceramic, in particular also zirconium oxide, aluminum oxide, yttrium oxide or mixtures thereof. Ceramics with their metal components originating from Group IVB (Ti and higher) or IIIA (Al and higher), are also well-suited for use as the insulating device.

Diverse techniques can be used to attach the insulating device to the distal end of the pipe section. In one embodiment, one method of attaching the insulating device, which is configured as a ceramic body, to the distal end of the pipe section includes placing a preformed green body on the distal end of the pipe section, the green body enclosing at least sections of said pipe section, and sintering the green body in such a manner that the shrinkage of the ceramic ensures a firm seat on the pipe section. Consequently, a "waste product", as it were, in the manufacture of the ceramic body, i.e., the shrinkage process, is utilized to ensure, at the same time, a firm connection with the pipe section bearing the insulating body. It has been found that, without any additional measures, the holding force of such a connection is particularly great.

BRIEF DESCRIPTION OF THE DRAWINGS

The disclosed embodiments will be described in greater detail, pointing out further features and advantages, by reference to the example embodiments illustrated in the drawings.

DETAILED DESCRIPTION

In the description hereinafter, the same reference signs are used for parts that are the same and for parts that have the same function.

Figure 1:
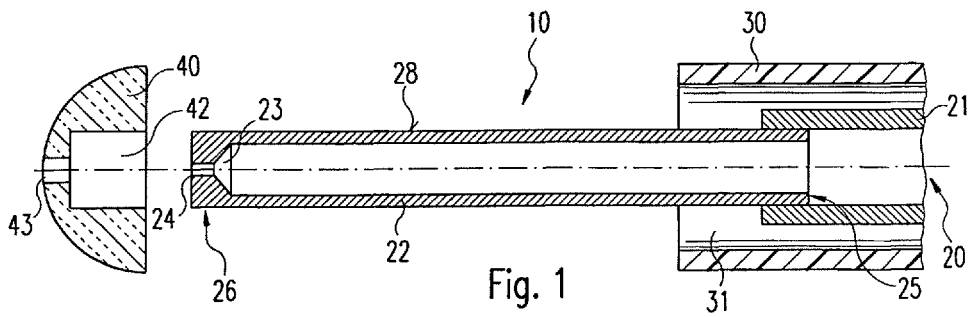
FIG. 1 illustrates a first disclosed embodiment, in semi-assembled state.

FIG. 1 shows a longitudinal section of a surgical instrument 10 in semi-assembled state. The surgical instrument includes a fluid jet device 20. In order to produce the fluid jet device 20, a supply line 21 is provided, the supply line 21 being connected with a (not illustrated) pump device for generating a high-pressure fluid.

The supply line 21 is connected to a proximal end 25 of a pipe section 22 in a sealed manner. Like the supply line 21, the pipe section 22 consists of an electrically conductive material, so that an electrical connection exists between the two lines.

Whereas the supply line 21 consists of a flexible (electrically conductive) material, the pipe section 22, preferably comprising tungsten, is sintered by means of a MIM process, i.e., this section is extremely stiff and resistant to burning off.

The pipe section 22 has a nozzle 23 on its distal end 26 that includes a relatively sharp-edged nozzle rim 24. Furthermore, reference sign 28 identifies a peripheral region of the pipe section 22 which—as will still be described farther below—is used as the cutting electrode (and, optionally, also for the coagulation of tissue). Component 28 is referred to as a "peripheral electrode".

Furthermore, an insulating device 40 is provided, said insulating device consisting of a ceramic, insulating material (such as zirconium oxide, aluminum oxide, yttrium oxide or mixtures thereof, or ceramics with their metal components originating from Group IVB (Ti and higher) or IIIA (Al and higher) produced by means of a CIM process. The insulating device 40 includes a pipe receiving opening 42 that is shaped to accommodate the distal end 36 of the pipe section 22. Molded to this pipe receiving opening 42 is an adjoining jet outlet 43 that has the shape of a pocket hole such that when the insulating device 40 is attached to the pipe section 22 or the distal end 26 of said pipe section, as shown in FIG. 2, there is enough room for a water jet exiting from the nozzle 23 to pass through.

Furthermore, a sheathing device 30, preferably an insulating biocompatible and temperature-resistant plastic tube, may be provided. The sheathing device 30 can be moved relative to the supply line 21 or to the pipe section 22—either, as shown in the upper half of FIG. 2, enclosing the pipe section 22, or, as shown in the lower half of FIG. 2, exposing the pipe section 22.

In doing so, the interior space or lumen of the sheathing device 30 can be used as line 31 through which the inert gas, in particular argon, can be conveyed into the region between the peripheral electrode 28 and the (not shown) tissue that is to be treated.

Figure 2:
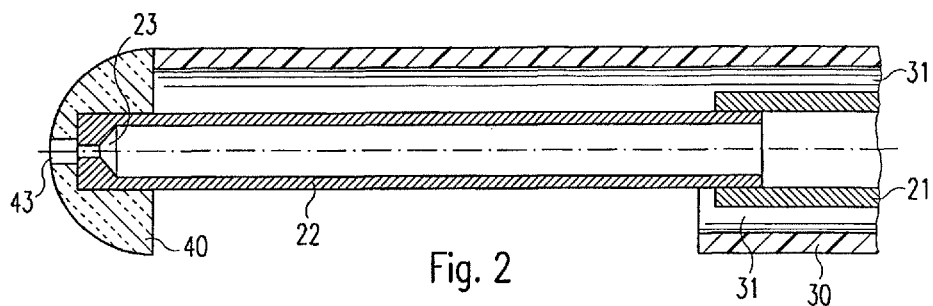
FIG. 2 illustrates the embodiment of FIG. 1 in an assembled state, where the upper half and the lower half of the arrangement show two different operating modes.
Figure 3:
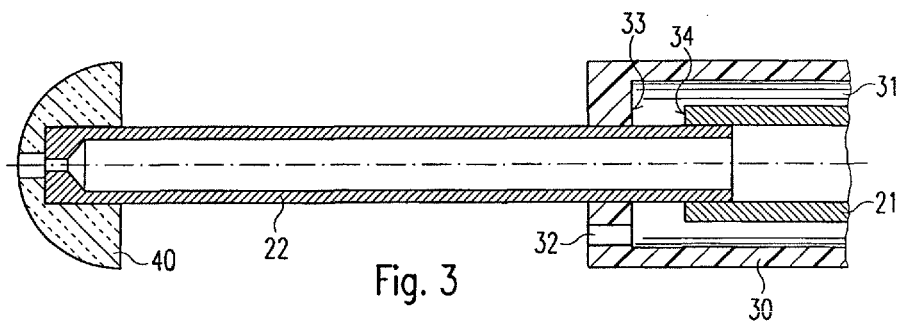
FIG. 3 illustrates another disclosed embodiment similar to that of FIGS. 1 and 2.
Figure 4:
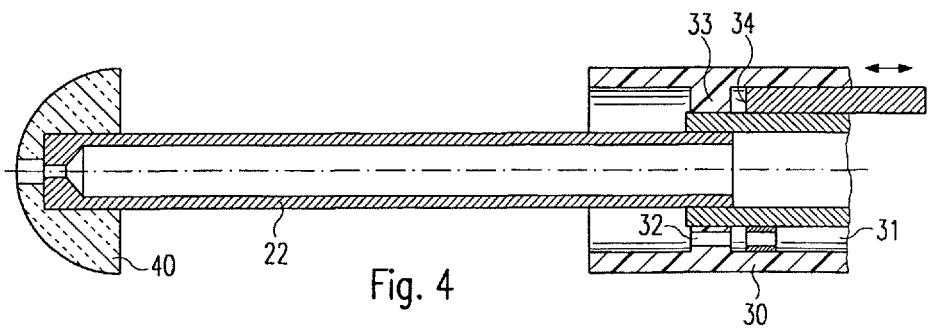
FIG. 4 illustrates another disclosed embodiment including stop devices.

The embodiments of FIGS. 3 and 4 differ from that of FIGS. 1 and 2 in that stop devices 33, 34 are provided in the embodiments of FIGS. 3 and 4. These stop devices allow the pipe section 22 to be moved out of the sheathing device 30 only over a limited range. In the embodiment shown in FIG. 3, the sheathing device 30 is closed on its end, with the exception of a passage for the pipe section 23. This "end wall" forms the first stop 33. The second stop 34 is formed by the supply line 21 or its distal end. In order to ensure—as before—a gas outflow from the line 31, an outflow opening 32 is provided in the "end wall" of the sheathing device 30.

In the embodiment of in FIG. 4, a special constriction is provided as the first stop 33 in the sheathing device 30. The second stop 34 is formed by an additional part that is seated on the supply line 21. This second stop 34 (as indicated by the double arrow in FIG. 4) can be moved in such a manner that the degree by which the pipe section 22 can be slid out of the sheathing device 30 and can be adjusted. Here, it should be noted that the dimensions shown in FIG. 4 do not fully correspond to optimal conditions.

Figure 5:
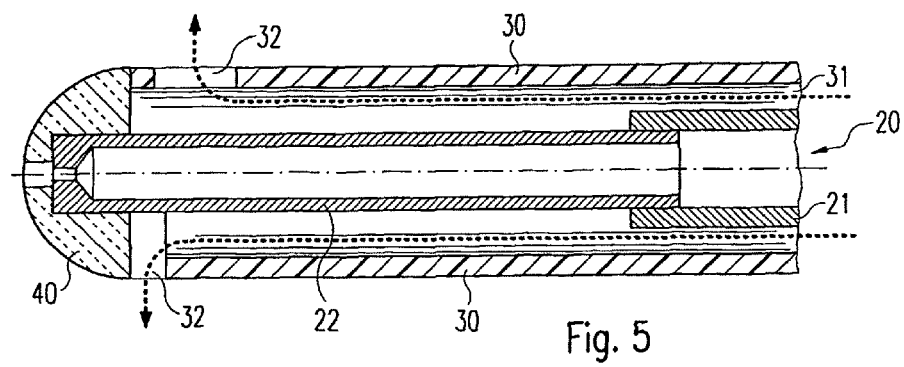
FIG. 5 illustrates another disclosed embodiment including an inert gas supply line in two different operating modes, as shown in the upper and lower halves, respectively.

The embodiment of FIG. 5 is different from the previously shown embodiments in that an additional outflow opening 32 (upper half of FIG. 5) is provided, where the inert gas flowing through the line 31 can flow out in lateral direction (as indicated by the dotted line). In the modification shown in the lower portion of FIG. 5, the arrangement is such that the outflow opening 32 is formed by a gap between a distal end rim of the sheathing device 30 and the insulating device 40 (where, also in this case, the gas flow is indicated by a dotted arrow).

Figure 6:
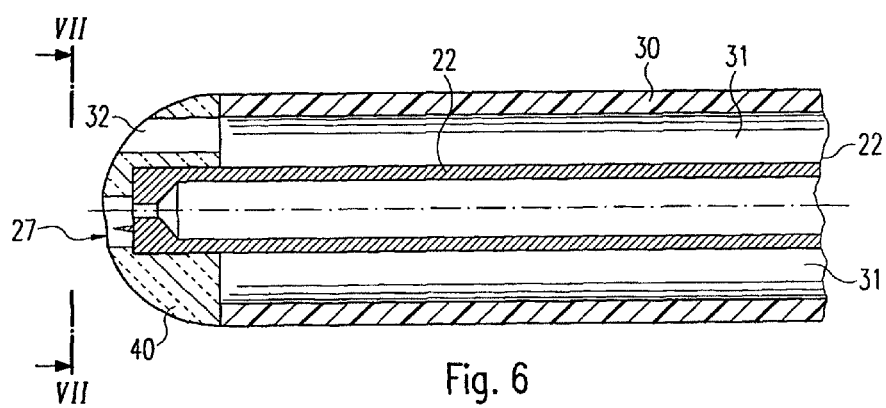
FIG. 6 illustrates another disclosed embodiment.
Figure 7:
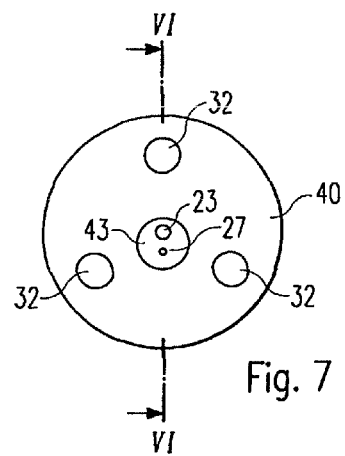
FIG. 7 illustrates a view of the embodiment of FIG. 6, along line VII-VII of FIG. 6.

The embodiment shown by FIGS. 6 and 7 is different from that of FIG. 5 in that the outflow opening 32 is configured for the outflow of an inert gas flowing through the line 31 out of three holes (see FIG. 7) that are provided in the insulating device 40.

Furthermore, the embodiment as in FIGS. 6 and 7 is different in that, on the distal end surface of the pipe section 22, there is a conical concentrating element 27 that is designed so as to form one part with the pipe section 22 (but may also be inserted).

The use of the instrument of the disclosed embodiments allows the implementation of three functions with the single instrument. Firstly, water jet surgery can be performed with the use of the water jet device. Secondly, an incision can be made by RF surgery, where a corresponding RF frequency current is supplied to the pipe section 22 and its circumference, i.e., the peripheral electrode 28, is brought into contact with tissue. To accomplish this, the insulating device 40 can be simultaneously used as a preparation instrument for mechanical preparation (e.g., opening) of tissue. Thirdly, a plasma coagulation can be performed, where an inert gas is conveyed through the line 31 and the outflow opening 32 in such a manner that the inert gas fills a region between the tissue to be coagulated and the distal end of the pipe section 22. If, then, an appropriately high RF voltage is applied via the supply line 21 and the pipe section 22, an RF discharge occurs with the development of a corresponding plasma between the tissue and those locations of the pipe section 22 where the field strength is particularly high. The electric field strength becomes particularly high at those locations that have beveled or pointed form (this is referred to as tip discharge). In the embodiments of FIGS. 1 through 5, this is usually the nozzle rim 24 because all other "beveled parts" of the pipe section 22 are either covered by the insulating device 40 or are too remote from the tissue. The exemplary embodiment of FIGS. 6 and 7 shows another increase of the field strength through the tip-shaped concentrating element 27. In order to make this possible, an enlarged jet outlet 43 is provided in the insulating device 40, said jet outlet being of such a size that the concentrating element 27 is exposed and that sufficient space is made available for the fluid jet to exit from the nozzle 23.

The description hereinabove shows that the present invention provides a highly compact combination or multifunction instrument that is particularly suitable for endoscopic operations.

It should be noted at this point that all the aforementioned parts are claimed as essential to the invention both alone and in any combination, particularly the details shown in the drawings. Amendments thereof are the common practice of persons skilled in the art.

The invention claimed is:

1. An endoscopic surgical instrument comprising:
    a fluid jet device comprising a pipe section with a nozzle on a distal end thereof for a dissection and/or a needleless injection by means of a fluid;
    an electrode device included in the pipe section, the electrode device for cutting and/or coagulating a tissue by means of RF current; and
    an insulating device attached to the distal end of the pipe section and configured to prevent electrically conductive contact between the tissue and the distal end of the pipe section.

2. The endoscopic surgical instrument of claim 1, wherein the insulating device is configured as a mechanical preparation device for the preparation of tissue.

3. The endoscopic surgical instrument of claim 1, further comprising a supply line for conveying an inert gas to the tissue.

4. The endoscopic surgical instrument of claim 3, wherein the electrode device further comprises a concentrating element arranged on the distal end of the pipe section in an aperture in the insulating device and having a beveled form to enhance a field strength generated by an electrical charge of the electrode device.

5. The endoscopic surgical instrument of claim 3, wherein the electrode device further comprises a concentrating element arranged on the distal end of the pipe section in an aperture in the insulating device and having a pointed form to enhance a field strength generated by an electrical charge of the electrode device.

6. The endoscopic surgical instrument of claim 1, further comprising a sheathing device arranged so as to movably enclose the electrode device such that the electrode device can be retracted into the sheathing device or projected out of said sheathing device.

7. The endoscopic surgical instrument of claim 6, further comprising stop devices arranged such that any retraction/projection of the electrode device is delimited by the stop devices.

8. The endoscopic surgical instrument of claim 7, wherein the stop devices are adjustable.

9. The endoscopic surgical instrument of claim 1, wherein the fluid jet device further comprises an electrically conductive supply line for supplying the fluid and the RF current, said electrically conductive supply line being in sealed and electrically conductive communication with the pipe section.

10. The endoscopic surgical instrument of claim 1, wherein the pipe section is made of a material having a melting point above 2000° C.

11. The endoscopic surgical instrument of claim 10, wherein the pipe section is made of tungsten.

12. The endoscopic surgical instrument of claim 11, wherein the pipe section is manufactured by a powder injection molding process.

13. The endoscopic surgical instrument of claim 1, wherein the insulating device is manufactured using a powder injection molding process.

14. The endoscopic surgical instrument of claim 1, wherein the insulating device is comprised of a ceramic.

15. The endoscopic surgical instrument of claim 14, wherein the insulating device is comprised of a material selected from the group consisting of zirconium oxide, aluminum oxide, yttrium oxide and mixtures thereof, or of ceramics having metal components originating from Group IVB (Ti and higher) or IIIA (Al and higher).

* * * * *